US008814357B2

(12) United States Patent
De Lemos (10) Patent No.: US 8,814,357 B2
(45) Date of Patent: *Aug. 26, 2014

(54) SYSTEM AND METHOD FOR IDENTIFYING THE EXISTENCE AND POSITION OF TEXT IN VISUAL MEDIA CONTENT AND FOR DETERMINING A SUBJECT'S INTERACTIONS WITH THE TEXT

(75) Inventor: Jakob De Lemos, Copenhagen V (DK)

(73) Assignee: iMotions A/S, Copenhagen (DK)

( * ) Notice: Subject to any disclaimer, the term of this patent is extended or adjusted under 35 U.S.C. 154(b) by 11 days.

This patent is subject to a terminal disclaimer.

(21) Appl. No.: 13/424,109

(22) Filed: Mar. 19, 2012

(65) Prior Publication Data

US 2012/0237084 A1   Sep. 20, 2012

Related U.S. Application Data

(63) Continuation of application No. 12/542,111, filed on Aug. 17, 2009, now Pat. No. 8,136,944.

(60) Provisional application No. 61/089,200, filed on Aug. 15, 2008.

(51) Int. Cl.
    *A61B 3/14*   (2006.01)
    *A61B 3/00*   (2006.01)
    *G06K 9/00*   (2006.01)

(52) U.S. Cl.
    USPC ............................. 351/209; 351/246; 382/103

(58) Field of Classification Search
    USPC ................................... 351/209, 210; 600/558
    See application file for complete search history.

(56) References Cited

U.S. PATENT DOCUMENTS 3,507,988 A    4/1970  Holmes
3,712,716 A    1/1973  Cornsweet et al. ............... 351/7

(Continued)

FOREIGN PATENT DOCUMENTS

EP    0 883 049 A1    12/1998
JP    H07-313494      12/1995

(Continued)

OTHER PUBLICATIONS

Crosby, Martha E., et al., "Physiological Data Feedback for Application in Distance Education", *ACM* 1-58113-448-7-11/14/01, PUI 2001, Orlando, Florida, copyright 2001, 5 pages.

(Continued)

*Primary Examiner* — Jordan Schwartz
(74) *Attorney, Agent, or Firm* — Pillsbury Winthrop Shaw Pittman LLP (57) ABSTRACT

A reading meter system and method is provided for identifying the existence and position of text in visual media content (e.g., a document to be displayed (or being displayed) on a computer monitor or other display device) and determining if a subject has interacted with the text and/or the level of the subject's interaction with the text (e.g., whether the subject looked at the text, whether the subject read the text, whether the subject comprehended the text, whether the subject perceived and made sense of the text, and/or other levels of the subject's interaction with the text). The determination may, for example, be based on data generated from an eye tracking device. The reading meter system may be used alone and/or in connection with an emotional response tool (e.g., a software-based tool for determining the subject's emotional response to the text and/or other elements of the visual media content on which the text appears). If used together, the reading meter system and emotional response tool advantageously may both receive, and perform processing on, eye date generated from a common eye tracking device.

5 Claims, 6 Drawing Sheets

(56) References Cited

U.S. PATENT DOCUMENTS

| | | | |
|---|---|---|---|
| 3,827,789 A | 8/1974 | Molner et al. ................... 351/23 |
| 3,986,030 A | 10/1976 | Teltscher ...................... 250/349 |
| 4,034,401 A | 7/1977 | Mann ............................ 358/93 |
| 4,075,657 A | 2/1978 | Weinblatt ...................... 358/93 |
| 4,146,311 A | 3/1979 | Murr ............................ 351/24 |
| 4,483,681 A | 11/1984 | Weinblatt ...................... 434/236 |
| 4,528,989 A | 7/1985 | Weinblatt ...................... 128/745 |
| 4,574,314 A | 3/1986 | Weinblatt ...................... 358/227 |
| 4,582,403 A | 4/1986 | Weinblatt ...................... 351/210 |
| 4,623,230 A | 11/1986 | Weinblatt ...................... 351/210 |
| 4,647,964 A | 3/1987 | Weinblatt ...................... 358/84 |
| 4,649,434 A | 3/1987 | Weinblatt ...................... 358/250 |
| 4,659,197 A | 4/1987 | Weinblatt ...................... 351/210 |
| 4,661,847 A | 4/1987 | Weinblatt ...................... 358/108 |
| 4,670,264 A | 6/1987 | Warren et al. ............... 424/195.1 |
| 4,670,463 A | 6/1987 | Warren et al. ............... 514/464 |
| 4,695,879 A | 9/1987 | Weinblatt ...................... 358/84 |
| 4,718,106 A | 1/1988 | Weinblatt ...................... 455/2 |
| 4,837,851 A | 6/1989 | Weinblatt ...................... 455/67 |
| 4,931,865 A | 6/1990 | Scarampi ...................... 358/84 |
| 4,974,010 A | 11/1990 | Cleveland et al. ............. 354/403 |
| 4,992,867 A | 2/1991 | Weinblatt ...................... 358/108 |
| 5,090,797 A | 2/1992 | Cleveland et al. ............. 351/210 |
| 5,202,355 A | 4/1993 | Nakatsu ........................ 514/568 |
| 5,204,703 A | 4/1993 | Hutchinson et al. .......... 351/210 |
| 5,219,322 A | 6/1993 | Weathers ...................... 600/27 |
| 5,231,674 A | 7/1993 | Cleveland et al. ............. 382/6 |
| 5,243,517 A | 9/1993 | Schmidt et al. ............. 364/419.2 |
| 5,318,442 A | 6/1994 | Jeffcoat et al. ............... 433/72 |
| 5,380,540 A | 1/1995 | Yamanaka et al. .......... 426/534 |
| 5,406,956 A | 4/1995 | Farwell ........................ 128/731 |
| 5,517,021 A | 5/1996 | Kaufman et al. .............. 250/221 |
| 5,617,855 A | 4/1997 | Waletzky et al. ............ 128/653.1 |
| 5,649,061 A | 7/1997 | Smyth ............................ 395/20 |
| 5,676,138 A | 10/1997 | Zawilinski .................... 128/630 |
| 5,725,472 A | 3/1998 | Weathers ...................... 600/21 |
| 5,884,626 A | 3/1999 | Kuroda et al. ................ 128/630 |
| 5,912,721 A | 6/1999 | Yamaguchi et al. ......... 351/210 |
| 6,021,346 A | 2/2000 | Ryu et al. ..................... 600/544 |
| 6,067,842 A | 5/2000 | Gygax et al. .................. 73/23.34 |
| 6,090,051 A | 7/2000 | Marshall ...................... 600/300 |
| 6,102,870 A | 8/2000 | Edwards ...................... 600/558 |
| 6,120,461 A | 9/2000 | Smyth .......................... 600/558 |
| 6,151,571 A | 11/2000 | Pertrushin .................... 704/209 |
| 6,163,281 A | 12/2000 | Torch ............................ 341/21 |
| 6,190,314 B1 | 2/2001 | Ark et al. ..................... 600/300 |
| 6,228,038 B1 | 5/2001 | Claessens .................... 600/558 |
| 6,275,806 B1 | 8/2001 | Pertrushin .................... 704/272 |
| 6,292,688 B1 | 9/2001 | Patton .......................... 600/544 |
| 6,298,263 B1 | 10/2001 | Sedgwick et al. ............ 600/544 |
| 6,346,887 B1 | 2/2002 | Van Orden et al. .......... 340/575 |
| 6,353,810 B1 | 3/2002 | Petrushin ...................... 704/236 |
| 6,385,590 B1 | 5/2002 | Levine .......................... 705/10 |
| 6,401,050 B1 | 6/2002 | Cooke et al. ................. 702/127 |
| 6,422,999 B1 | 7/2002 | Hill |
| 6,427,137 B2 | 7/2002 | Petrushin ...................... 704/273 |
| 6,429,868 B1 | 8/2002 | Dehner, Jr. et al. ........... 345/440 |
| 6,434,419 B1 | 8/2002 | Gevins et al. ................. 600/544 |
| 6,453,194 B1 | 9/2002 | Hill .............................. 600/546 |
| 6,463,415 B2 | 10/2002 | St. John ...................... 704/273 |
| 6,463,786 B1 | 10/2002 | Behan et al. ................. 73/23.34 |
| 6,480,826 B2 | 11/2002 | Petrushin ...................... 704/270 |
| 6,572,562 B2 | 6/2003 | Marshall ...................... 600/558 |
| 6,585,521 B1 | 7/2003 | Obrador ....................... 434/236 |
| 6,598,971 B2 | 7/2003 | Cleveland ...................... 351/209 |
| 6,638,217 B1 | 10/2003 | Liberman ..................... 600/300 |
| 6,697,457 B2 | 2/2004 | Petrushin ..................... 379/88.08 |
| 6,826,540 B1 | 11/2004 | Plantec et al. ................. 705/10 |
| 6,862,497 B2 | 3/2005 | Kemp et al. .................. 700/264 |
| 6,873,314 B1 | 3/2005 | Campbell ..................... 345/156 |
| 6,879,709 B2 | 4/2005 | Tian et al. .................... 382/118 |
| 6,978,243 B2 | 12/2005 | Godinot et al. ............... 705/1 |
| 7,027,621 B1 | 4/2006 | Prokoski ....................... 382/118 |
| 7,110,582 B1 | 9/2006 | Hay .............................. 382/128 |
| 7,113,916 B1 | 9/2006 | Hill .............................. 705/10 |
| 7,120,880 B1 | 10/2006 | Dryer et al. ................... 715/863 |
| 7,155,159 B1 | 12/2006 | Weinblatt et al. ............. 455/2.01 |
| 7,191,403 B2 | 3/2007 | Crain et al. ................... 715/760 |
| 7,246,081 B2 | 7/2007 | Hill .............................. 705/10 |
| 7,302,475 B2 | 11/2007 | Gold et al. ................... 709/217 |
| 7,306,337 B2 | 12/2007 | Ji et al. ......................... 351/209 |
| 7,356,470 B2 | 4/2008 | Roth et al. .................... 704/270 |
| 7,401,920 B1 | 7/2008 | Kranz et al. .................. 351/210 |
| 7,593,952 B2 | 9/2009 | Soll et al. ..................... 707/102 |
| 7,657,062 B2 | 2/2010 | Pilu .............................. 382/103 |
| 7,689,499 B1 | 3/2010 | Duquette ...................... 705/37 |
| 7,740,631 B2 | 6/2010 | Bleich et al. .................. 606/79 |
| 7,747,068 B1 | 6/2010 | Smyth et al. .................. 382/154 |
| 7,881,493 B1* | 2/2011 | Edwards et al. .............. 382/103 |
| 8,136,944 B2* | 3/2012 | De Lemos .................... 351/209 |
| 2002/0007105 A1 | 1/2002 | Prabhu et al. ................ 600/26 |
| 2002/0037533 A1 | 3/2002 | Civelli et al. ................. 435/7.1 |
| 2002/0091654 A1 | 7/2002 | Alroy ............................ 706/21 |
| 2002/0105427 A1 | 8/2002 | Hamamoto et al. .......... 340/576 |
| 2002/0133347 A1 | 9/2002 | Schoneburg et al. ......... 704/257 |
| 2002/0135618 A1 | 9/2002 | Maes et al. ................... 345/767 |
| 2003/0001846 A1 | 1/2003 | Davis et al. .................. 345/474 |
| 2003/0040921 A1 | 2/2003 | Hughes et al. ............... 705/1 |
| 2003/0046401 A1 | 3/2003 | Abbott et al. ................ 709/228 |
| 2003/0078838 A1 | 4/2003 | Szmanda ..................... 705/14 |
| 2003/0123027 A1 | 7/2003 | Amir et al. ................... 351/209 |
| 2003/0125610 A1 | 7/2003 | Sachs et al. .................. 600/300 |
| 2004/0009462 A1 | 1/2004 | McElwrath .................. 434/350 |
| 2004/0044495 A1 | 3/2004 | Lampert et al. .............. 702/127 |
| 2004/0092809 A1 | 5/2004 | DeCharms .................... 600/410 |
| 2004/0098298 A1 | 5/2004 | Yin .............................. 705/10 |
| 2004/0193068 A1 | 9/2004 | Burton et al. ................ 600/544 |
| 2004/0210159 A1 | 10/2004 | Kibar ............................ 600/558 |
| 2004/0249650 A1 | 12/2004 | Freedman et al. ............ 705/1 |
| 2005/0075532 A1 | 4/2005 | Lee et al. ..................... 600/27 |
| 2005/0132290 A1 | 6/2005 | Buchner et al. .............. 715/702 |
| 2005/0175218 A1 | 8/2005 | Vertegaal et al. ............. 382/103 |
| 2005/0221268 A1 | 10/2005 | Chaar et al. .................. 434/350 |
| 2005/0225723 A1 | 10/2005 | Pilu .............................. 351/209 |
| 2005/0228785 A1 | 10/2005 | Wolcott et al. ............... 707/3 |
| 2005/0234779 A1 | 10/2005 | Chiu et al. .................... 705/24 |
| 2005/0289582 A1 | 12/2005 | Tavares et al. ................ 725/10 |
| 2006/0030907 A1 | 2/2006 | McNew ....................... 607/88 |
| 2006/0049957 A1 | 3/2006 | Surgenor et al. ........ 340/825.19 |
| 2006/0064037 A1 | 3/2006 | Shalon et al. ................ 600/586 |
| 2006/0074742 A1 | 4/2006 | Santandrea .................. 705/10 |
| 2006/0082206 A1 | 4/2006 | Travis ......................... 297/423.1 |
| 2006/0110008 A1 | 5/2006 | Vertegaal et al. ............. 382/103 |
| 2006/0167371 A1 | 7/2006 | Flaherty et al. .............. 600/545 |
| 2006/0167530 A1 | 7/2006 | Flaherty et al. .............. 607/62 |
| 2006/0189900 A1 | 8/2006 | Flaherty ....................... 600/595 |
| 2006/0241356 A1 | 10/2006 | Flaherty ....................... 600/301 |
| 2006/0293948 A1 | 12/2006 | Weinblatt ..................... 705/14 |
| 2006/0294537 A1 | 12/2006 | Weinblatt ..................... 725/10 |
| 2007/0066916 A1* | 3/2007 | Lemos ......................... 600/558 |
| 2007/0097234 A1 | 5/2007 | Katayama .................... 348/239 |
| 2007/0097319 A1 | 5/2007 | McKay et al. ................ 353/7 |
| 2007/0100666 A1 | 5/2007 | Stivoric et al. ............... 705/3 |
| 2007/0123794 A1 | 5/2007 | Togino ........................ 600/558 |
| 2007/0150916 A1 | 6/2007 | Begole et al. ................ 725/10 |
| 2007/0167690 A1 | 7/2007 | Miyazaki et al. ............ 600/300 |
| 2007/0260127 A1 | 11/2007 | El-Nokaly et al. .......... 600/301 |
| 2007/0265507 A1 | 11/2007 | De Lemos ................... 600/300 |
| 2007/0273611 A1 | 11/2007 | Torch ........................... 345/8 |
| 2007/0282912 A1 | 12/2007 | Reiner ......................... 707/104.1 |
| 2007/0287881 A1 | 12/2007 | Akimov et al. .............. 600/26 |
| 2007/0300174 A1 | 12/2007 | Macbeth et al. .............. 715/772 |
| 2008/0043013 A1 | 2/2008 | Gruttadauria et al. ........ 345/419 |
| 2008/0065468 A1 | 3/2008 | Berg et al. .................... 705/10 |
| 2008/0071136 A1 | 3/2008 | Oohashi et al. .............. 600/27 |
| 2008/0146890 A1 | 6/2008 | LeBoeuf et al. .............. 600/300 |
| 2008/0255949 A1 | 10/2008 | Genco et al. ................. 705/14 |
| 2009/0030287 A1 | 1/2009 | Pradeep et al. ............... 600/300 |
| 2009/0270170 A1 | 10/2009 | Patton .......................... 463/36 |
| 2010/0004977 A1* | 1/2010 | Marci et al. .................. 705/10 |
| 2010/0010317 A1* | 1/2010 | De Lemos ................... 600/300 |

(56) References Cited

U.S. PATENT DOCUMENTS

| | | | |
|---|---|---|---|
| 2010/0010370 A1* | 1/2010 | De Lemos et al. | 600/558 |
| 2010/0039618 A1 | 2/2010 | De Lemos | 351/209 |
| 2012/0078065 A1 | 3/2012 | De Lemos et al. | 600/301 |

FOREIGN PATENT DOCUMENTS

| | | |
|---|---|---|
| JP | 11014510 | 1/1999 |
| JP | 2006-325756 | 12/2006 |
| WO | WO 90/02543 | 3/1990 |
| WO | WO 97/33515 | 9/1997 |
| WO | WO 97/38624 | 10/1997 |
| WO | WO 99/24159 | 5/1999 |
| WO | WO 03/105786 | 12/2003 |
| WO | WO 2005/032503 | 4/2005 |
| WO | WO 2005/043453 | 5/2005 |
| WO | WO 2006/111476 | 10/2006 |
| WO | WO 2007/096706 | 8/2007 |
| WO | WO 2007/102053 | 9/2007 |
| WO | WO 2008/014346 | 1/2008 |
| WO | WO 2008/023260 | 2/2008 |
| WO | WO 2008/129356 | 10/2008 |
| WO | WO 2010/004426 | 1/2010 |
| WO | WO 2010/004429 | 1/2010 |
| WO | WO 2010/018459 | 2/2010 |
| WO | WO 2010/100567 | 10/2010 |

OTHER PUBLICATIONS

Jackson, Daren C., et al., "Now You Feel It, Now You Don't: Frontal Brain Electrical Asymmetry and Individual Differences in Emotion Regulation", *Physiological Science*, vol. 14, No. 6, Nov. 2003, pp. 612-617.

Lang, Peter J., "International Affective Picture System (IAPS): Instruction Manual and Affective Ratings", *Technical Report A-6*, The Center for Research in Psychophysiology, University of Florida, 2005, 56 pages.

Papert, Seymour, et al., "Computer Tracking of Eye Motions", *Artificial Intelligence Memo No. 123*, Vision Memo, Massachusetts Institute of Technology, Project MAC, Mar. 1967, 5 pages.

Schubert, Emery, "Emotionface: Prototype Facial Expression Display of Emotion in Music", *Proceedings of ICAD 04-Tenth Meeting of the International Conference on Auditory Display*, Sydney, Australia, Jul. 6-9, 2004, 1 page.

"Did-it, Enquiro, and Eyetools Uncover Google?s Golden Triangle", Anonymous, Mar. 1, 2005, the URL for this story is http://www.eye-tracking.info/modules.php?name=News&file=article&sid=8, 3 pages.

Taylor, J. G., et al., "Modelling the Interaction of Attention and Emotion", *BICS 2004*, Aug. 29-Sep. 1, 2004, Department of Mathematics, King's College, 4 pages.

TOBII Technology, Product Description, Tobii 1750 Eye-Tracker, Release B, Release Date: Nov. 2003, 16 pages.

TOBII Technology, Product Description, ClearView 2, Eye Gaze Analysis Software, Version 2.0, Sep. 2003, 16 pages.

TOBII Technology, Product Description, ClearView 2, Eye-Gaze Analysis Software (describing Release 2.1, Jan. 2004), Copyright 2003, 16 pages.

Bojko, Agnieszka, "Eye Tracking in User Experience Testing: How to Make the Most of It", *Proceedings of the UPA 2005 Conference*, 9 pages.

Yartz, Andrew R., et al., "Addressing the Specificity of Affective Startle Modulation: Fear Versus Disgust", *Biological Psychology*, vol. 59, 2002, pp. 55-68.

Duric et al., "Integrating Perceptual and Cognitive Modeling for Adaptive and Intelligent Human-Computer Interaction", *Proceedings of the IEEE*, vol. 90, No. 7, Jul. 2002, XP011065033, pp. 1272-1289.

Zhai et al., "Realization of Stress Detection Using Psychophysiological Signals for Improvement of Human-Computer Interaction", Southeastcon, 2005, *Proceedings, IEEE*, Ft. Lauderdale, Florida, Apr. 8-10, 2005, XP010789761, pp. 415-420.

Ioannou et al., "Emotion Recognition Through Facial Expression Analysis Based on a Neurofuzzy Network", *Neural Networks*, Elsevier Science Publishers, vol. 18, No. 4, May 2005, XP004965788, pp. 423-435.

Lien et al., "Detection, Tracking, and Classification of Action Units in Facial Expression", *Robotics and Autonomous Systems*, Elsevier Science Publishers, vol. 31, No. 3, May 2000, XP004197692, pp. 131-146.

Ikehara et al., "Assessing Cognitive Load with Physiological Sensors", *Proceedings of the 38$^{th}$ Hawaii International Conference on System Sciences*, Jan. 3, 2005, XP010762783, pp. 295A-1-295A-9.

Partala, Timo et al., "Pupil Size Variation as an Indication of Affective Processing", *International Journal of Human-Computer Studies*, vol. 59, Issues 1-2, Jul. 2003, pp. 185-198.

Nold, Christian, "Bio Mapping", Jan. 2004, www.biomapping.net. 15 pages.

Geirsson, Halldor, "Detection of Outliers", Mar. 21, 2003, hraun.vedur.is/ja/skyrslur/contgps/node1.html, 3 pages.

Alaoui-Ismaili, O. et al., "Odor Hedonics: Connection with Emotional Response Estimated by Automatic Parameters", Oxford University Press, pp. 237-248, 1997.

Alata, Mohanad et al., "Text Detection and Character Recognition Using Fuzzy Image Processing", *Journal of Electrical Engineering*, vol. 57, No. 5, 2006, pp. 258-267.

Campbell, Christopher et al., "A Robust Algorithm for Reading Detection", *PUI 2001*, Orlando, Florida, 7 pages.

Goldberg, Joseph et al., "Eye Tracking in Web Search Tasks: Design Implications", ETRA '02, New Orleans, Louisiana, 2002, pp. 51-58.

ISCAN Incorporated, "Magnetic Resonance Remote Eye Tracking Laboratory", Eye & Target Tracking Instrumentation, 2000, 2 pages.

ISCAN Incorporated, "ETL-300 Binocular Free-Head Eye Tracking Laboratory", Eye & Target Tracking Instrumentation, 2000, 4 pages.

ISCAN Incorporated, "ETL-400 Tabletop Remote Eye Tracking Laboratory", Eye & Target Tracking Instrumentation, 2000, 4 pages.

ISCAN Incorporated, "ETL-500 Head-Mounted Eye Tracking Laboratory", Eye & Target Tracking Instrumentation, 2000, 4 pages.

Niemic, Christopher et al., "Studies of Emotion, A Theoretical and Emperical Review of Psychophysiological Studies of Emotion", jur.rochester.edu, vol. 1, Issue 1, Fall 2002, pp. 15-18.

Pan, Bing et al., "The Determinants of Web Page Viewing Behavior: An Eye-Tracking Study", Association for Computing Machinery, Inc., 2004, pp. 147-154.

Rupp, Heather et al., "Sex Differences in Viewing Sexual Stimuli: An Eye-Tracking Study in Men and Women", *Hormones and Behavior*, vol. 51, 2007, pp. 524-533.

Schnipke, Susan et al., "Trials and Tribulations of Using an Eye-Tracking System", CHI 2000, Apr. 1-6, 2000, pp. 273-274.

Spillers, Frank, Demystifying Usability: Eye-Tracking Studies—Usability Holy Grail?, http://experiencedynamics.blogs.com/site_search_usability/2004/12/eyetracking_stu.html, printed Dec. 7, 2007, 10 pages.

Visual Impact Test—Eye Tracking—Emotional Response—Visual Attention—Eyetracking, Black Box Global Research, printed from http://blackboxglobal.com/visual-impact.html, printed Dec. 7, 2007, 3 pages.

Brave et al., The Human-Computer Interaction Handbook, 2002, pp. 87-88.

Geirsson et al., "Continuous GPS Measurements in Iceland 1999-2002", published Mar. 2003, Chapter 3.2 "Detection of Outliers", 92 pages.

Ebrahimi, Touradj et al., "Brain-Computer Interface in Multimedia Communication", *IEEE Signal Processing Magazine*, Jan. 2003, IEEE Press, USA, pp. 14-24.

(56) References Cited

OTHER PUBLICATIONS

Hayashi, Hidehiko, et al., "Eye Movement Tracking to Support the Second Language Learners' Self-Learning in Comprehension of English Texts", *2002 IEEE International Conference on Systems, Man and Cybernetics*, vol. 7, Oct. 9, 2002, XP-002562615, 6 pages.

Brosch, Tobias, et al., "The Perception and Categorisation of Emotional Stimuli: A Review", *Cognition and Emotion*, vol. 24, No. 3, Jan. 1, 2010, pp. 377-400.

Bradley, Margaret M., et al., "The Pupil as a Measure of Emotional Arousal and Autonomic Activation", *Psychophysiology*, vol. 45, available online Feb. 12, 2008, pp. 602-607.

International Search Report and Written Opinion mailed Feb. 3, 2010 in International Application No. PCT/IB2009/006756, 14 pages.

Reply to Written Opinion filed Jun. 14, 2010 in International Application No. PCT/IB2009/006756, 4 pages.

International Preliminary Report on Patentability mailed Nov. 16, 2010 in International Application No. PCT/IB2009/006756, 6 pages.

\* cited by examiner

Reading Example:

This person is reading the text for understanding. So even though not every word is fixated, the amount of time spent on each word is indicative of the processing of the word.

Skimming Example:

This person is skimming the text. This is most obvious from the pattern of fixations that are more dispersed and shorter fixation durations that is typical for this type of reading. The main gist maybe understood, but poorer memory for the text usually results.

Publish one coupon per month (6 total) on the SloobyBucks page in UWeekly. 20,000 copies of your coupon get in front of our 50,000 weekly readers! UW has established itself as the #1 campus area paper, among readers and advertisers. UW students prefer UWeekly over The Lantern!
Value: $65 per month

1  Readers: 10/13
        Read (%): 53%

FIG. 6A

You receive 10 days of text ads per month (60 total) to promote your business on uweekly.com. These highly effective ads run across the entire uweekly.com website and receive 5-10,000 views daily! It is one of the highest traffic local websites with over 50,000 visitors/50,000 pageviews/mo.
Value: $65 per month

2  Readers: 9/13
        Read (%): 43%

FIG. 6B

Sloopybucks.com lets you create up to 10 coupons that users can save, print and email. They can also enter key biz info, upload and create and manage your Text Ads.

3  Readers: 4/13
        Read (%): 92%

FIG. 6C

Sloopybucks.com is the new, "go-to" site for local coupons with over $30,000 in marketing behind it.
Value: $35 per month

4  Readers: 1/13
        Read (%): 83%

FIG. 6D

SYSTEM AND METHOD FOR IDENTIFYING THE EXISTENCE AND POSITION OF TEXT IN VISUAL MEDIA CONTENT AND FOR DETERMINING A SUBJECT'S INTERACTIONS WITH THE TEXT

CROSS-REFERENCE TO RELATED APPLICATIONS

This application is a continuation of U.S. patent application Ser. No. 12/542,111, filed Aug. 17, 2009 (now U.S. Pat. No. 8,136,944 B2, issued Mar. 20, 2012), which claims priority to U.S. Provisional Patent Application Ser. No. 61/089,200, filed Aug. 15, 2008, each of which is hereby incorporated by reference herein in its entirety.

FIELD OF THE INVENTION

The invention relates to a system and method for identifying the existence and position of text in visual media content, and for determining whether a subject has interacted with the text and/or the level of the subject's interaction with the text based on, for example, data generated from an eye tracking device.

BACKGROUND OF THE INVENTION

Systems for determining whether a user has looked at text on a display are generally known. These systems, however, have a number of limitations and drawbacks. For example, there is a difference between simply determining whether a user's eyes have passed over text, and determining whether the user has interacted with the text and, if so, the level of the subject's interaction with the text (e.g., whether the user actually read and/or comprehended the text).

Additionally, while some text identification tools exist, these tools too suffer from various limitations and drawbacks.

SUMMARY OF THE INVENTION

The invention addressing these and other drawbacks in the art relates to a reading meter system and method for identifying the existence and position of text in visual media content (e.g., a document or other visual media content to be displayed (or being displayed) on a computer monitor or other display device) and determining whether a subject has interacted with the text and/or the level of the subject's interaction with the text (e.g., whether the subject looked at the text, whether the subject read the text, whether the subject comprehended the text, whether the subject perceived and made sense of the identified text, and/or other levels of the subject's interaction with the text). The determination may, for example, be based on eye data generated from an eye tracking device. Eye data may include, but not be limited to, pupil data, blink data, gaze data, eye position/movement, pupil dilation, and/or other eye data.

The reading meter system may be used alone and/or in connection with an emotional response tool (e.g., a software-based tool for determining the subject's emotional response to the text and/or other elements of the visual media content on which the text appears). If used together, the reading meter system and emotional response tool advantageously may both receive, and perform processing on, eye data generated from a common eye tracking device.

According to one implementation of the invention, the reading meter system may comprise a general purpose computer programmed with a reading meter software application and/or a software-based emotional response test, an eye tracking device, a computer monitor or other display device (or virtual display), one or more input devices, one or more output devices, and/or other system components.

The reading meter software application may comprise one or more of a text identification and position determination module, an eye gaze pattern determination module, a text interaction determination module, a cognitive workload determination module, a memory impact determination module, and/or other modules as described herein.

The text identification and position determination module may comprise one or more sub-modules for identifying the existence of text in visual media content, identifying the position of the identified text, and identifying geometry (or geometrical) characteristics of the identified text, and/or for performing other functions.

The text identification module may identify some or all of the text in visual media content. The text may be identified based on blocks of text and/or portions thereof such as, for example, paragraphs, sentences, phrases, words, and/or other portions.

The text position identification module may identify the position (e.g., x-y or other coordinates) of an identified portion of the text in relation to the visual media content in which it appears (e.g., a document that includes both text and other display elements).

The text geometry characteristics module may identify various characteristics (or attributes) of identified text including, but not limited to, text character height, text character width, text character font, number of letters, number of words, length of words, length of lines of text, number of lines of text, etc. Various Optical Character Recognition (OCR) (or other) techniques may be implemented by the text geometry characteristics module to identify one or more of the aforementioned characteristics.

The identification of a text portion and its position may be performed manually, automatically, and/or semi-automatically. The text identification and position determination module may direct the storage of information regarding the identified portions of text, their respective positions in a given piece of visual media content, and/or the characteristics of the identified portions of text. Such information may be stored in a text identification and position database, or other storage mechanism.

According to an aspect of the invention, the eye gaze pattern determination module may be operable to determine a subject's eye gaze pattern based on collected eye gaze data. For example, the eye gaze pattern determination module may receive eye gaze data (for one or both eyes) from an eye tracking device, wherein such data indicates the position (e.g., x-y or other coordinates) on a computer (or other) display at which a subject's eye(s) looked at a particular sample time. Based on a time series of such eye position data (e.g., at a predetermined sampling rate), the eye gaze pattern determination module can determine the subject's eye gaze pattern (e.g., the positions of the visual media content at which the user looked over some time) in relation to the coordinates of the visual media content being displayed. The eye gaze pattern determination module may direct the storage of eye gaze pattern information for a subject's interaction with a given piece of visual media content. Such information may be stored in an eye gaze pattern database, or other storage mechanism.

The eye gaze pattern determination module may account for the distance between the subject's eye(s) and the displayed visual media content, as this distance affects a subject's gaze pattern while reading. This distance may be measured automatically, or manually and input by the subject or a test administrator. The focal vision is the center of vision and covers a circle of ca. two degrees around the gaze point. Focal vision allows the subject to see clearly and to read. When an object is moved away from the eye, for example, the focal vision covers a larger area of the object on the cost of resolution, that is, the retinal image becomes smaller. This influences the saccade length and the ability and ease of reading a text. Reading saccades span, on average, about two degrees of visual angle, although this can be better expressed in terms of a span of 7 to 9 letter spaces, since the number of letters covered remains largely invariant despite differences in text size or distance.

The eye gaze pattern determination module may receive data from the text identification and position determination module to account for changes in, for example, text block sizes, font sizes, word length, and word complexity, among other things, as these may affect a subject's gaze pattern while reading.

The text interaction determination module may process information (e.g., the text identification/position information, the eye gaze pattern information, and/or other information) to determine, for example, whether the subject has interacted with the text in the visual media content, and/or the level of the subject's interaction with the text. For example, upon processing some or all of the foregoing information, if the text interaction determination module determines that at least some of the coordinate positions of an identified text block in the visual media content coincide with at least some of the coordinate positions of a subject's gaze (e.g., based on eye gaze pattern information), the text interaction determination module may determine that the subject has interacted with the identified text. Based on this, and/or other processing, additional information can be determined. For example, the eye gaze pattern of the subject may be effectively superimposed on to the visual media content to determine information regarding the subject's level of interaction with the identified text. Information regarding the subject's level of interaction with the identified text may include, for example, whether the subject looked at the identified text, whether the subject read the identified text, whether the subject comprehended the identified text, whether the subject perceived and made sense of the identified text, and/or other levels of interaction. The text interaction determination module may direct the storage of information regarding the subject's interactions with the identified text in a given piece of visual media content. Such information may be stored in a text interaction database, or other storage mechanism.

The text interaction determination module may comprise one or more sub-modules for reading determination, comprehension determination, and/or other functions. The reading determination module may determine if the subject read the identified text. The comprehension determination module may determine if the subject comprehended the identified text.

According to one aspect of the invention, the cognitive workload determination module may monitor the environment, stimulus (e.g., document, visual media content, and/or other stimulus), and/or subject to determine workload on the subject continuously to provide information on when the subject has the spare capacity to receive and comprehend the text during text interaction. The workload determination may be based on pupilometrics and/or gaze patterns.

According to one aspect of the invention, the memory impact determination module may receive data from the cognitive workload determination module and the eye gaze pattern determination module to identify current words of interest which attract special attention (e.g., direction of sight, longer duration of fixations, or returning to particular parts of the text). Since the reading process is mainly cognitive, there is a direct link between gaze patterns while reading and the processing in working memory.

In one implementation of the invention, the emotional response tool may include a software application running on the same (or another computer) as the reading meter software application. The emotional response tool software application may include an emotional response determination module, a visual attention determination module, and/or other modules.

The emotional response determination module may determine information regarding the subject's emotional response to the visual media content, or portions of the visual media content (e.g., one or more portions of the identified text, images and/or other portions of the visual media content). The emotional response may include, for example, the direction (valence) and magnitude (arousal) of any emotional response.

The visual attention determination module may determine visual attention information for the subject. Visual attention information may include, for example, information regarding points or areas of the visual media content on which the subject focused for at least a minimum amount of time, information regarding points or areas of the visual media content on which the subject re-focused on or returned to (e.g., return points), and/or other information. The visual attention information may indicate the points or areas of the visual media content that drew and/or held the subject's attention. The emotional response determination module and visual attention determination module may direct the storage of information regarding the subject's emotional response and visual attention. Such information may be stored in an emotional response and visual attention database, or other storage mechanism.

According to one implementation of the invention, in operation, visual media content may be displayed to a subject (or user) via a computer monitor or other display device. The visual media content may comprise a stimulus or other piece(s) of content, in any format (e.g., on a slide), which may include various display elements, at least a portion of which may include text.

Assuming the visual media content includes a portion of text, the text identification and position determination module may identify the existence and position of text (absolute or relative to other display elements) in the visual media content at any time (e.g., when presented, or before or after presentation). Various eye property data from a subject positioned before the display may be acquired (e.g., by an eye tracking device associated with the monitor). The eye data may be collected at a predetermined sampling rate. The eye data may include eye position data, eye blink data, pupil dilation data and/or other eye data. Other physiological data, and/or other data may be collected (e.g., by a data collection module). Data concerning one or more physiological attributes of the subject may be collected from one or more emotion detection sensors, and/or one or more environmental parameters (e.g., light intensity, noise, temperature, and/or other parameters) may also be measured and collected.

An exemplary (and non-limiting) description of the set-up and calibration of an eye tracking device and other sensors (along with data collection and analysis) is described in detail in U.S. Patent Application Publication No. 2007/0066916A1, published Mar. 22, 2007, which is hereby incorporated herein by reference in its entirety.

The eye data collected (and/or other collected information), may be used, for example, by the eye gaze pattern determination module to determine the eye gaze pattern(s) of the subject. The text identification and position data, the eye gaze pattern data, and/or other collected data may be provided as input to the text interaction determination module. The text interaction module may determine whether the subject has interacted with the identified text and/or the level of the subject's interactions with the text (e.g., whether the subject looked at the identified text, whether the subject read the identified text, whether the subject comprehended the identified text, whether the subject perceived and made sense of the identified text, and/or other levels of interaction), and/or other portions of the display. If desired, visual attention and/or emotional response may also be determined. The results of the analysis may be stored and/or output in a variety of formats.

Various other objects, features, and advantages of the invention will be apparent through the detailed description of the preferred embodiments and the drawings attached hereto. It is also to be understood that both the foregoing general description and the following detailed description are exemplary and not restrictive of the scope of the invention.

BRIEF DESCRIPTION OF THE DRAWINGS

FIG. 2 is a schematic block diagram illustrating exemplary (and non-limiting) features and functionality of a text identification and position determination module and an eye gaze pattern determination module, as well as the communication there-between.

DETAILED DESCRIPTION OF THE INVENTION

Figure 1:
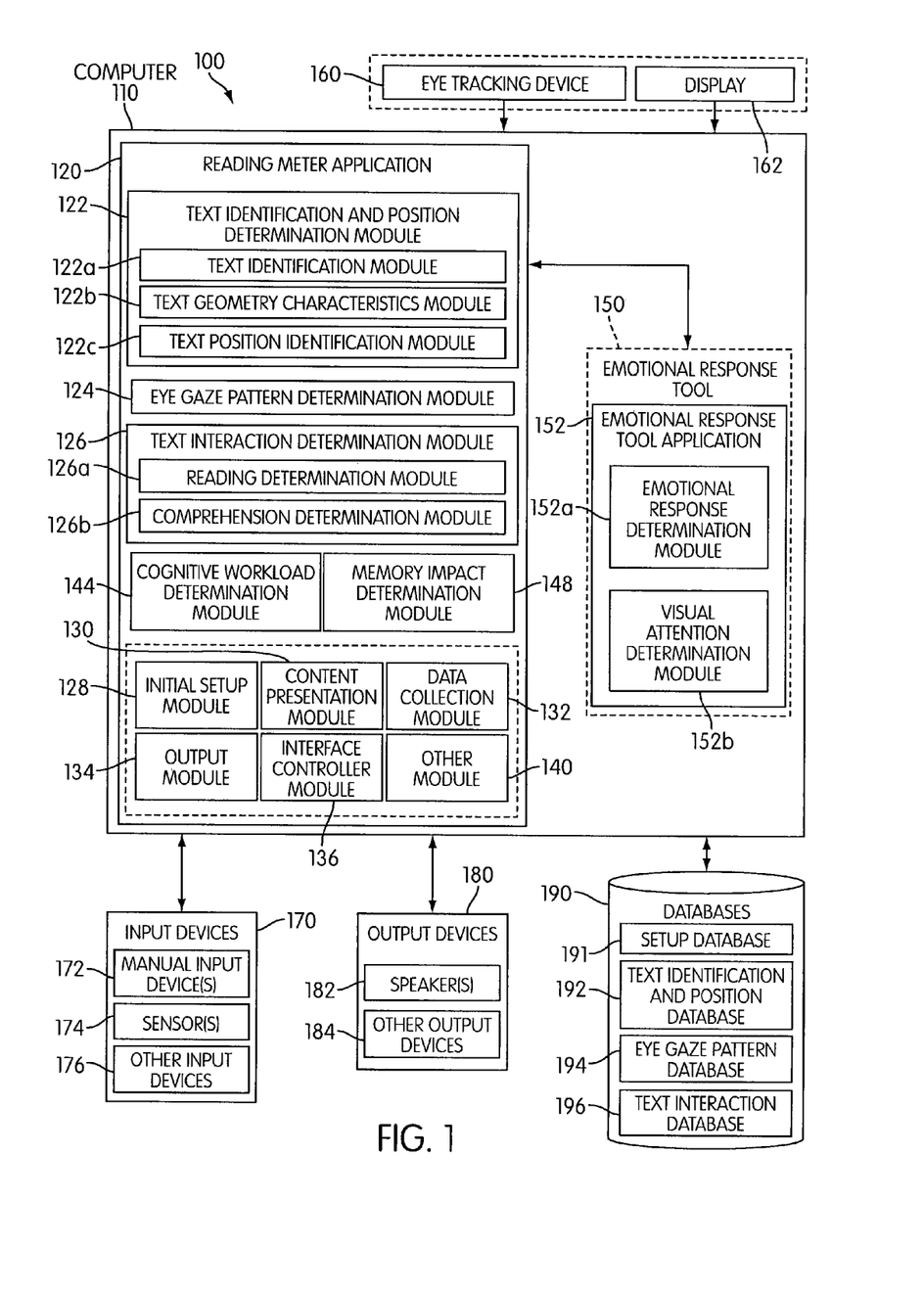
FIG. 1 is an exemplary illustration of a reading meter system, according to an aspect of the invention.

According to one implementation of the invention, as shown for example in FIG. 1, a reading meter system 100 may comprise a general purpose computer 110 programmed with a reading meter software application 120, an eye tracking device 160, a computer monitor or other display device (or virtual display) 162, one or more input devices 170, one or more output devices 180, one or more and/or other components. Computer 110 may comprise a processor (not shown), circuitry and/or other hardware operable to execute computer-readable instructions. According to an aspect of the invention, computer 110 may include one or more computer-readable storage media configured to store one or more software modules, wherein the software modules include computer-readable instructions that when executed by the processor cause the processor to perform the functions described herein.

The reading meter software application 120 may comprise one or more software modules that enable various features and functions of the invention. Non-limiting examples of the software modules may include one or more of a text identification and position determination module 122, an eye gaze pattern determination module 124, a text interaction determination module 126, a cognitive workload determination module 144, a memory impact determination module 148, and/or other modules.

The text identification and position determination module 122 may comprise one or more sub-modules for text identification 122a, text geometry characteristics 122b, text position identification 122c, and/or for performing other functions. The text identification module 122a may identify some or all of the text in visual media content. The text may be identified based on blocks of text and or portions thereof such as, for example, paragraphs, sentences, phrases, words, and or other portions.

Various known text identification techniques may be used by text identification module 122a to identify text in visual media content. For example, the text identification module 122a may use the image processing techniques discussed in article titled "Text Detection and Character Recognition using Fuzzy Image Processing", by Alata et al., which is hereby incorporated by reference herein in its entirety, to detect and recognize text in a document image.

Text position identification module 122c may identify the position (e.g., x-y or other coordinates) of an identified portion of the text in relation to the visual media content in which it appears (e.g., a document that includes both text and other display elements).

The text geometry characteristics module 122b may identify various characteristics (or attributes) of identified text including, but not limited to, text character height, text character width, text character font, number of letters, number of words, length of words, length of lines of text, number of lines of text, etc. As previously noted, various Optical Character Recognition (OCR) (or other) techniques may be implemented by text geometry characteristics module 122b to identify one or more of the aforementioned characteristics.

The identification of a text portion and its position may be performed manually, automatically, and/or semi-automatically. The text identification and position determination module 122 may direct the storage of information regarding the identified portions of text, their respective positions in a given document, and/or the characteristics of the identified portions of text. Such information may be stored in a text identification and position database 192, or other storage mechanism.

The eye gaze pattern determination module 124 may be operable to determine a subject's eye gaze pattern based on collected eye gaze data (e.g., generated by eye tracking device 160). For example, the gaze pattern determination module may receive eye gaze data (for one or both eyes) from eye tracking device 160, wherein such data indicates the position (e.g., x-y or other coordinates) on a computer (or other) display at which a subject's eye(s) looked at a particular sample time. Based on a time series of such eye position data (e.g., at a predetermined sampling rate), the eye gaze pattern determination module 124 can determine the subject's eye gaze pattern (e.g. the positions of the document at which the user looked over some time) in relation to the coordinates of the document being displayed. The eye gaze pattern determination module 124 may direct the storage of eye gaze pattern information for a subject's interaction with a given piece of visual media content. Such information may be stored in an eye gaze pattern database 193, or other storage mechanism.

The eye gaze pattern determination module may account for the distance between the subject's eye(s) and the displayed visual media content, as this distance affects a subject's gaze pattern while reading. This distance may be measured automatically, or manually and input by the subject or a test administrator. The focal vision is the center of vision and covers a circle of ca. two degrees around the gaze point. Focal vision allows the subject to see clearly and to read. When an object is moved away from the eye, for example, the focal vision covers a larger area of the object on the cost of resolution, that is, the retinal image becomes smaller. This influences the saccade length and the ability and ease of reading a text. Reading saccades span, on average, about two degrees of visual angle, although this can be better expressed in terms of a span of 7 to 9 letter spaces, since the number of letters covered remains largely invariant despite differences in text size or distance.

Figure 2:
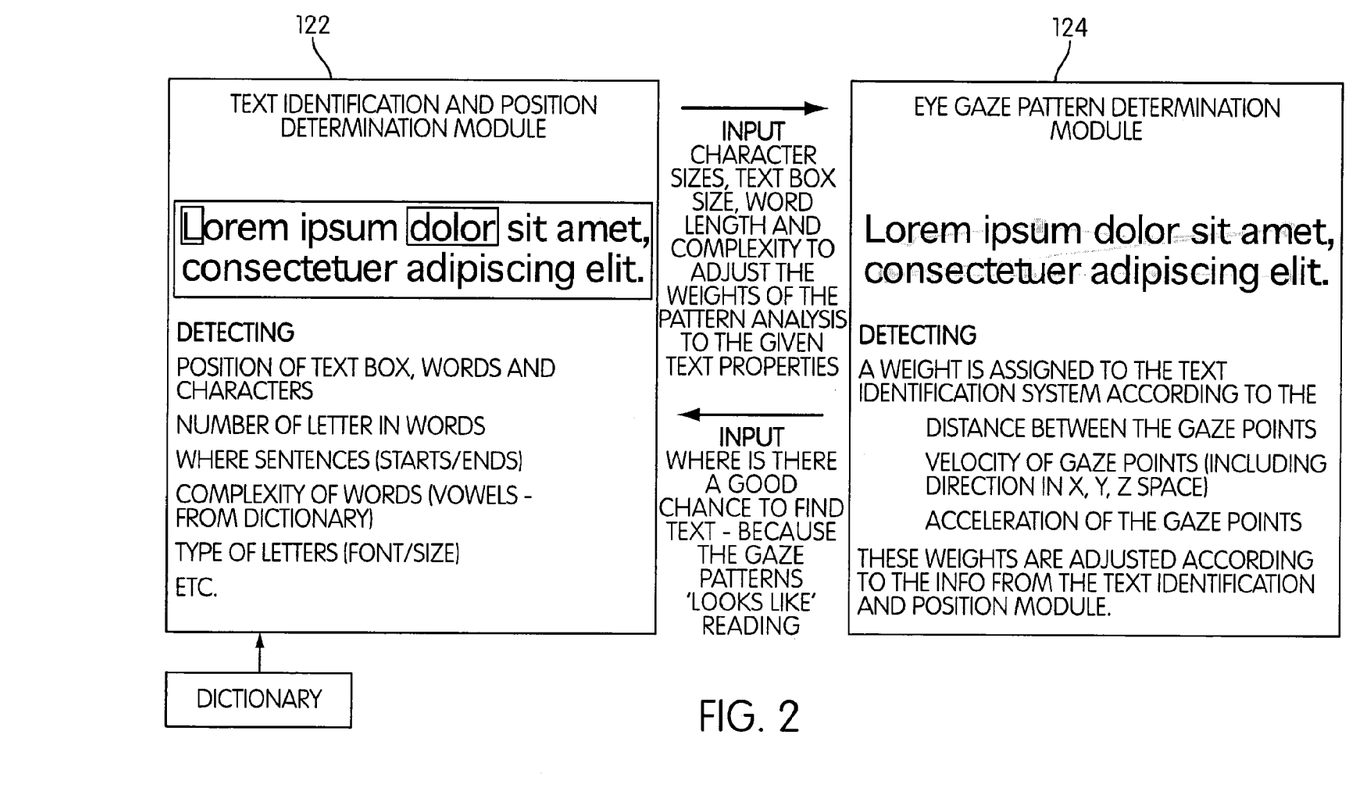

The eye gaze pattern determination module 124 may receive data from the text identification and position determination module 122 to account for changes in, for example, text block sizes, font sizes, word length, and word complexity, among other things, as these may affect a subject's gaze pattern while reading. FIG. 2 is a schematic block diagram illustrating exemplary (and non-limiting) features and functionality of text identification and position determination module 122 and eye gaze pattern determination module 124, as well as the communication there-between.

The eye gaze pattern determination module 124 may receive as input one or more properties/characteristics of the identified text from text identification and position determination module 122 to optimize the gaze analysis. The one or more properties may include, but not be limited to, text location, text size, character size, text box size, length of words, text complexity, number of lines of text, vertical interval between lines, color of text, contrast, font type, orientation (x, y, z, t in dynamic content), lix number (readability index), language (using for example input from a dictionary), start/end of sentences, and/or other text properties. The input may be utilized to distinguish, for example, reading from skimming as skimming could be interpreted as reading longer words or words with greater horizontal distance. The performance of the system may be improved by adjusting weights/thresholds of the pattern analysis to the given text properties.

According to an aspect of the invention, text identification and position determination module 122 may provide properties associated with the visual media content as input to eye gaze pattern determination module 124. Based on the input, it may be possible to distinguish between different text types, distinguish non-text portions from text portions, and/or perform other determinations, thereby improving gaze analysis and preventing non-text portions to be classified as read. For example, in some cases gaze patterns associated with non-text portions of visual media content may be similar to reading patterns which would give a false positive. In these cases, providing properties associated with visual media content as input to the eye gaze pattern determination module 124 may optimize gaze analysis. In order to support the text identification and position determination module 122 in text recognition, a preliminary output from eye gaze pattern determination module 124 may be used to indicate where there is a good chance of finding text because gaze patterns look like reading. According to an aspect of the invention, the preliminary output from eye gaze pattern determination module 124 may be used to indicate whether the subject gazed at an area of the visual media content. Text identification and position determination module 122 may perform text recognition in areas indicated by eye gaze pattern determination module 124.

Figure 3:
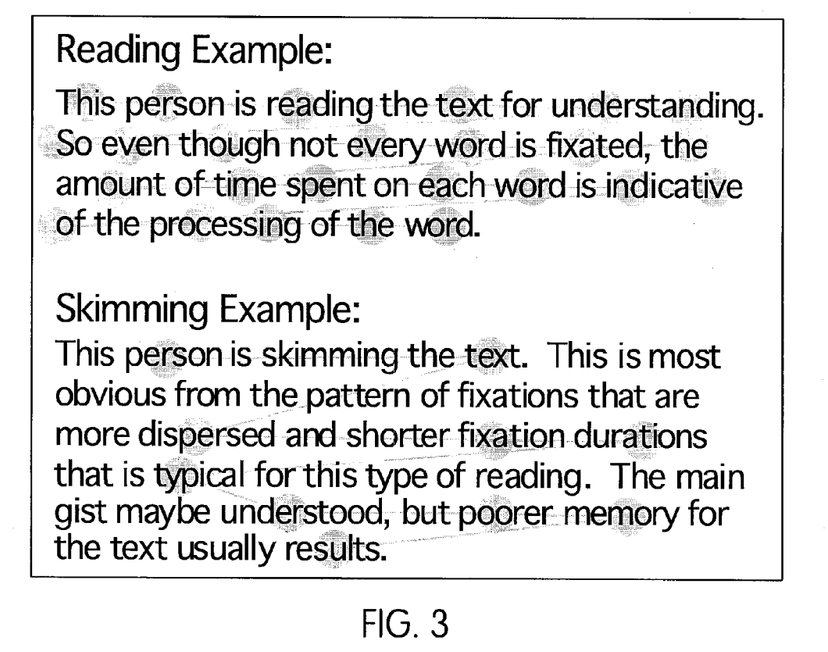
FIG. 3 is an exemplary illustration of an eye gaze pattern for an example wherein a user reads text (reading example), and an eye gaze pattern for an example wherein a user skims text (skimming example).

The text interaction determination module 126 may process the text identification/position information and the eye gaze pattern information to determine, for example, whether the subject has interacted with the text in the visual media content, and/or the level of the subject's interaction with the text. For example, by processing the foregoing data, if the text interaction determination module 126 determines that the coordinate positions of identified text in the document coincide with at least some of the coordinate positions of a subject's gaze (e.g., based on eye gaze pattern information), the text interaction determination module 126 may determine that the subject has interacted with the identified text. Based on this, and/or other processing, additional information can be determined. For example, the eye gaze pattern of the subject may be effectively superimposed on to the visual media content to determine information regarding the subject's level of interaction with the identified text. Information regarding the subject's level of interaction with the identified text may include, whether the subject looked at the identified text, whether the subject read the identified text, whether the subject comprehended the identified text, whether the subject perceived and made sense of the identified text, and/or other levels of interaction. FIG. 3 is an exemplary illustration of an eye gaze pattern for an example wherein a user reads text (reading example), and an eye gaze pattern for an example wherein a user skims text (skimming example).

The text interaction determination module 126 may direct the storage of information regarding the subject's interactions with the identified text in a given document. Such information may be stored in a text interaction database 194, or other storage mechanism.

If the text interaction determination module 126 determines that, for example, at least a portion of the subject's eye gaze pattern overlaps with the coordinate positions of identified text in the document, the text interaction determination module 126 may determine that the subject has interacted with the identified text, at least to some extent. This may mean that, at a minimum, the subject looked at the identified text.

The text interaction determination module 126 may comprise one or more sub-modules for reading determination 126a, comprehension determination 126b, and/or for performing other functions. The reading determination module 126a may determine whether the subject read the identified text. Various techniques (e.g., reading pattern templates) may be used by reading determination module 126a to determine whether the subject read the identified text.

According to one aspect of the invention, a subject's eye gaze pattern may be analyzed to determine if the subject's eye movements correlate with a reading pattern. As one example, in many languages a reading pattern may include eye movement from left to right, then back to the left and down (e.g., at the end of a line). If there is a correlation between a stored reading pattern and the subject's eye movements, it may be determined that the subject has read the identified text. Because people read at different rates, subject profile information may be used to calibrate and/or normalize data.

According to an aspect of the invention, attributes relating to a subject's interaction with the text (e.g., speed, acceleration, and direction of eye movements) may, in part, be used to determine if the subject read the identified text. A subject's eye gaze pattern information may be analyzed to determine the speed at which the subject interacted with the text. For example, quick eye movements (micro saccades) may indicate that the subject only skimmed through the text and did not read it.

The comprehension determination module 126b may determine whether the subject comprehended the identified text. The speed at which the subject interacted with the text, and/or the uniformity of the speed at which the subject interacted with the text may, in part, also determine if the subject comprehended the text or had difficulty comprehending the text. For example, while reading the text at a certain speed, if the subject had to slow down or revisit one or more portions of text (i.e. the speed at which the subject is interacting with text decreases), it may be determined that the subject had difficulty comprehending the text or portions thereof.

According to one aspect of the invention, the subject's emotional response information may also be used, either alone or in combination with the speed information, to determine if the subject comprehended the text. For example, the emotional response of the subject may indicate that the subject is confused or irritated, which in turn may indicate that the subject had difficulty comprehending the text.

The eye tracking device 160 may include a camera or other known eye-tracking device that records and tracks data relating to various eye properties of the subject. Examples of eye property data that may be collected may include eye position data, eye blink data, pupil dilation data, and/or other eye data.

Display 162 may comprise a physical display (e.g., a computer monitor comprising one or more Cathode Ray Tube (CRT) displays, digital flat panel displays or other display devices) or a virtual display (e.g., a multi-screen chamber like the CAVE sold by Fakespace Systems Inc.) for presenting visual instructions and messages, documents (e.g., slides or stimuli which may include various display elements, at least a portion of which may include text), and/or other information to subjects.

One or more input devices 170 may comprise one or more of manual input device(s) 172, sensors(s) 174, and/or other input devices 176 to receive input (e.g., from subjects). Manual input device(s) 172 may include one or more of a keyboard, mouse, and/or other input device that may enable subjects to manually input data. Sensor(s) 174 may include one or more emotional detection sensors, environmental sensors, and/or other sensors.

Emotion detection sensors may comprise, for example, one or more physiological sensors such as galvanic skin response sensors, facial recognition sensors, and/or other emotion detection sensors that may detect various physiological responses from subjects.

Environmental sensors may comprise, for example, one or more light intensity sensors, background noise sensors, temperature sensors, and/or other sensors that may measure various environmental parameters.

One or more output devices 180 may include one or more of speaker 182, and/or other output devices 184 (e.g., a printer). Speaker 182 may comprise one or more speakers for audible reproduction of, for example, audio instructions or messages, and/or other information to subjects.

According to one aspect of the invention, the reading meter software application 120 may further comprise one or more of an initial setup module 128, a content presentation module 130, a data collection module 132, an output module 134, an interface controller module 136, and/or other modules 140.

The initial setup module 128 may perform various setup/calibration functions. Examples of these functions may include, among other things, test/visual media content setup, subject setup, various calibration functions, or other functions. A test including one or more pieces of visual media content to be presented to the subject may be selected via the initial setup module 128. The one or more pieces of visual media content may include various types of elements, including text.

Visual media content presentation properties may be selected by initial setup module 128. For example, for a given test, one or more of the duration of presentation for various pieces of content may be selected along with the order of presentation of content, whether any content should be simultaneously presented, and/or other content presentation properties. Output presentation properties, for example, output presentation format, amount of information to be presented, and/or other output presentation properties, may be specified by initial setup module 128. Who should receive the output, how should the output be received, etc. may also be specified.

Various profile information regarding a subject may be collected by the initial setup module 128 including, but not limited to, name, age, gender, and/or other profile information. Various calibration protocols may be implemented by the initial setup module 128 including, for example, one or more calibration protocols for adjusting various sensors to an environment, adjusting various sensors to a subject within the environment, and determining a baseline emotional level for the subject within the environment.

Additional details on these and other calibration and initial setup functions that may be performed by initial setup module 128 are discussed in U.S. application Ser. No. 11/522,476, entitled "System and Method for Determining Human Emotion by Analyzing Eye Properties," filed Sep. 18, 2006, and in U.S. application Ser. No. 12/170,059, entitled "System and Method for Calibrating and Normalizing Eye Date in Emotional Testing," filed on Jul. 9, 2008, the disclosures of which are hereby incorporated by reference in their entireties.

The initial setup module 128 may direct storage of the setup information in setup database 191, or other storage mechanism.

The content presentation module 130 may facilitate the presentation of the visual media content.

The data collection module 132 may govern the collection of various eye property data from eye tracking device 160. The eye property data may include eye position data, eye blink data, pupil dilation data, and/or other eye data.

Data collection module 132 may further govern the collection of various physiological data, and/or other data. Data concerning one or more physiological attributes of the subject may be collected from one or more emotion detection sensors, and/or other sensors.

Data collection module 132 may collect various environmental parameters (e.g., light intensity, noise, temperature, and/or other environmental parameters) that may be measured by one or more environment sensors. The data collection module 132 may direct storage of the collected data in a collected data database 195.

In one implementation, the output module 134 may selectively enable various types of output to the one or more output devices 180. For example, output module 134 may be used to produce reports based on the results of various analyses of data described herein. Various electronic and/or printed output types may be used to present the results. These output types may include representation in the form of graphs, text, illustrations, gaze plots, audio, and/or video playback, or other output types.

Figure 6A:
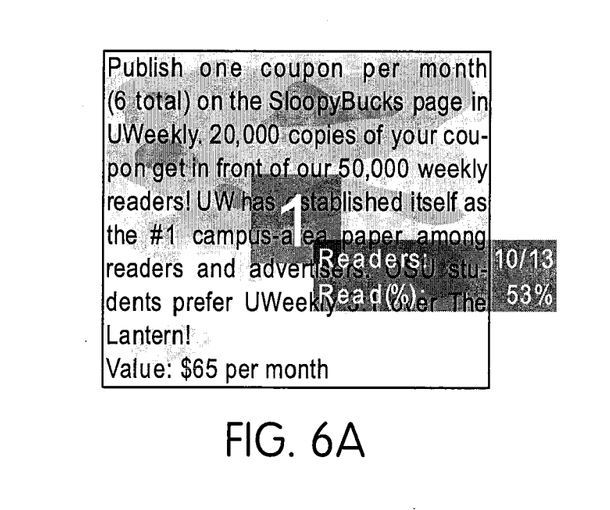
FIGS. 6A to 6D depict exemplary output charts/plots that may be presented, according to an aspect of the invention.

FIGS. 6A to 6D depict exemplary outputs that may be presented by output module 134. The number of subjects who have read the identified text out of a total number of subjects may be indicated by "Readers". The average amount of identified text read by the subjects may be indicated by Read (%). For example, the number of subjects who read the identified text of FIG. 6A is 10 out of a total number of 13 subjects. Also, the average amount of text read by the subjects is 53%. FIGS. 6A to 6D depict a Reading Intensity Map which may illustrate both what has been read (by one or more subjects) and the reading intensity. Reading intensity is a measure of how much time subjects spent reading a particular part of the text. An area which attracted more than 60% of the reading time may be marked as high reading intensity area (which is depicted as the darkest shade of gray in the figures). Most subjects have read the text in this area, and it may be an indicator that either the text is very attention grabbing, or unusual or difficult to read which is why subjects have spent much time there. Medium reading intensity depicted as a lighter shade of gray in the figures (lighter than the high reading intensity shade but darker than a low reading intensity shade) marks an area where 30-60% of the time was spent. These areas may have been read by around half the subjects. Low reading intensity areas have attracted less than 30% of the reading time, and are depicted by the lightest shade of gray in the figures. These areas may have only been read by a couple of subjects.

Figure 6B:
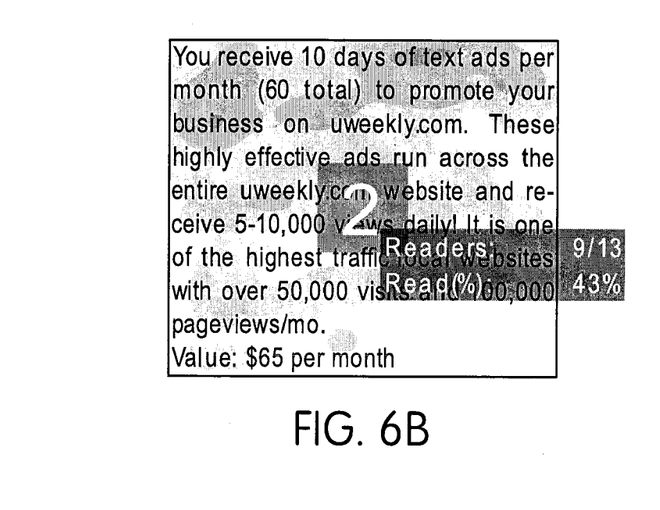
Figure 6C:
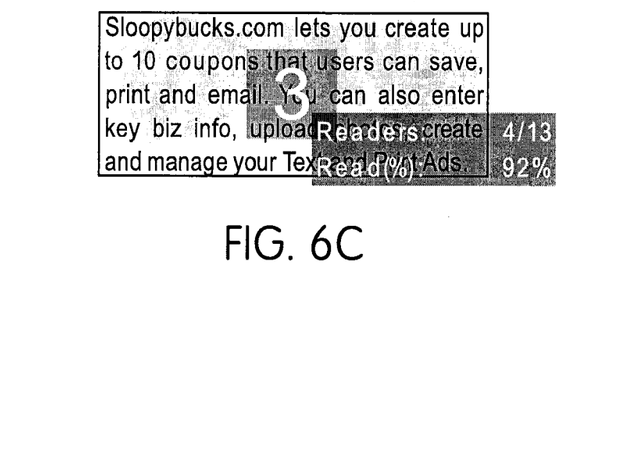
Figure 6D:
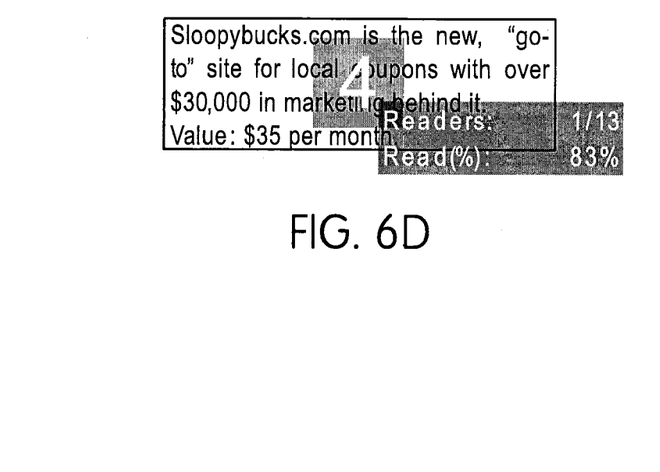

It may be seen in FIG. 6A, for example, that the words "SloopyBucks", "UWeekly" and "UW" have achieved a high reading intensity. These are all uncommon words, and thus subjects have dwelled longer on these words. In FIG. 6B, the portion "10 days of text ads per month" is bold text, which grabbed the subjects' attention, and raised the reading intensity. Reading intensity is normalized in each figure by the ratio of readers to the total number of subjects. This means that an area which has very few readers may have no Intensity map, as depicted in FIG. 6D for example. This may be helpful to easily identify the most and least read parts of visual media content. The numbers (e.g., 1, 2, 3, and 4) assigned to the text in FIGS. 6A to 6D may depend on the number of readers and/or how much they read.

The interface controller module 136 may be associated with and/or in communication with the one or more input devices, the one or more output devices, and/or other devices.

According to one aspect of the invention, reading meter system 100 may be used alone and/or in connection with emotional response tool 150. If used together, reading meter system 100 and emotional response tool 150 advantageously may both receive, and perform processing on, eye data generated by a common eye tracking device (e.g., eye tracking device 160). The emotional response tool 150 may include an emotional response tool software application 152 running on the same (or another) computer 110. The emotional response tool software application 152 may include one or more software modules that enable various features and functions of the invention. Non-limiting examples of the software modules may include one or more of an emotional response determination module 152a, a visual attention determination module 152b, and/or other modules.

In various implementations, information determined from one or more modules of emotional response tool software application 152 may be used as input for one or more processing operations performed by one or more modules of reading meter application 120, and vice versa.

In one implementation, the emotional response determination module 152a may determine information regarding the subject's emotional responses to visual media content, one or more portions of identified text, and/or other portions of a given piece of visual media content. Emotional response determination module 152a may analyze and process the eye data from eye tracking device 160 to determine the emotional response. The emotional response may include, for example, the direction (valence) and magnitude (arousal) of any emotional response.

The visual attention determination module 152b may determine visual attention information for the subject. Visual attention information may include, for example, information regarding points or areas of the document on which the subject focused for at least a minimum amount of time, information regarding points or areas of the documents on which the subject re-focused on or returned to (e.g., return points), and/or other information. The visual attention information may indicate points or areas of the visual media content that drew and/or held a subject's attention. Visual attention determination module 152b and/or text interaction determination module 126 may measure an amount of time one or more subjects spent reading a particular part of the text which may be referred to as reading intensity. The emotional response determination module 152a and visual attention determination module 152b may direct the storage of information regarding the subject's emotional response and visual attention. Such information may be stored in an emotional response and visual attention database 196, or other storage mechanism.

Additional details regarding the emotional response determination and visual attention determination are disclosed in U.S. application Ser. No. 11/522,476, filed Sep. 18, 2006; U.S. application Ser. No. 11/685,552, filed Mar. 13, 2007; U.S. application Ser. No. 12/170,059, filed Jul. 9, 2008; and U.S. application Ser. No. 12/170,041, filed Jul. 9, 2008, which are incorporated herein by reference in their entirety.

According to an aspect of the invention, cognitive workload determination module 144 may monitor the environment, stimulus, and/or subject to determine workload on the subject continuously to provide information on when the subject has the spare capacity to receive and comprehend the text during text interaction. The workload determination may be based on pupilometrics and/or gaze patterns.

Memory impact determination module 148 may receive data from the cognitive workload determination module and the eye gaze pattern determination module to identify current words of interest which attract special attention (e.g., direction of sight, longer duration of fixations, or returning to particular parts of the text). Since the reading process is mainly cognitive, there is a direct link between gaze patterns while reading and the processing in working memory.

According to an aspect of the invention, cognitive workload determination module 144 and/or memory impact determination module 148 may determine whether a subject perceived or made sense of the identified text.

Figure 4:
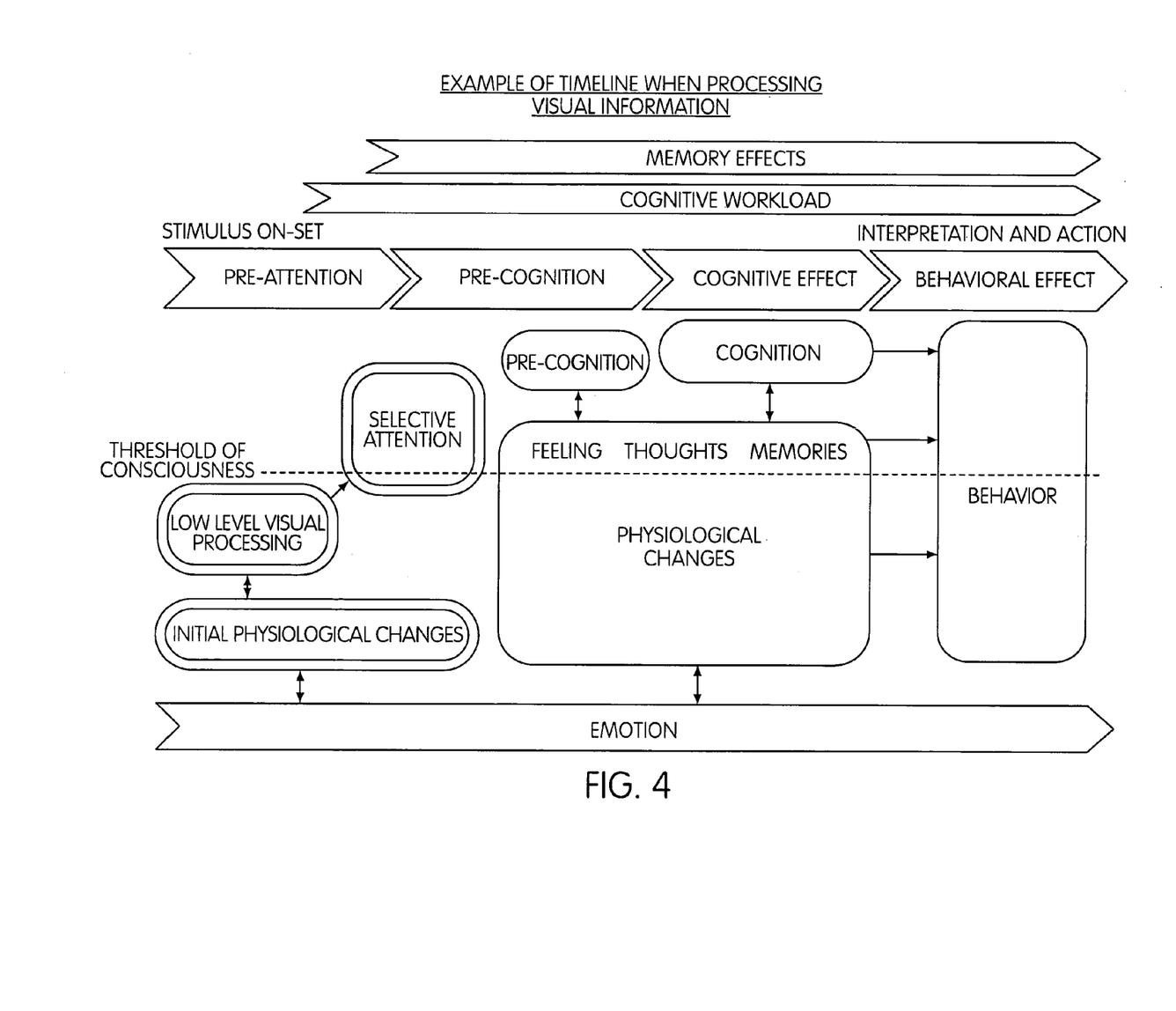
FIG. 4 is an exemplary illustration of timeline when processing visual information, according to an aspect of the invention.

FIG. 4 is an exemplary illustration of timeline when processing visual information and how it influences behavior, according to an aspect of the invention. The timeline includes one or more steps, for example, pre-attention, pre-cognition, cognitive effect, behavioral effect, and/or other steps. These steps may be influenced and guided by emotions. In the pre-attention step, for example, a stimulus (for example, visual media content) may initiate certain physiological and chemical changes in the body of a subject, These changes may influence low-level attention, and initiate emotions that may be triggered in the body together with the particular physiological changes that belong to those emotions, The emotions may guide selective attention. Low-level attention is automated and may subconsciously scan the whole visual field and spot the eye-catchers-the visual elements that catch attention. This is the part of attention that is automatic, involuntary and subconscious driven by emotions. Selective attention moves like a spotlight from one area of the visual field to another, analyzing the elements in more detail. Selective attention moves according to some attention values being calculated from partly the stimulus itself and partly by what is in the subject's mind, including emotions. Emotions participate in guiding and qualifying visual attention.

Together with the result of the selective attention, the emotions and physiological processes initiate pre-cognition. Pre-cognition may include non-verbal information, the potential for thoughts and images, and/or other information. Cognition, emotions and their respective physiological changes manifest into cognition and feelings. Feelings are part of emotions and physiological processes that become conscious. Cognition (thinking) and feelings are conscious phenomena that may influence behavior (for example, buying behavior, and/or other behavior). Behavior is, in other words, influenced by both subconscious emotions, cognition and feelings.

Figure 5:
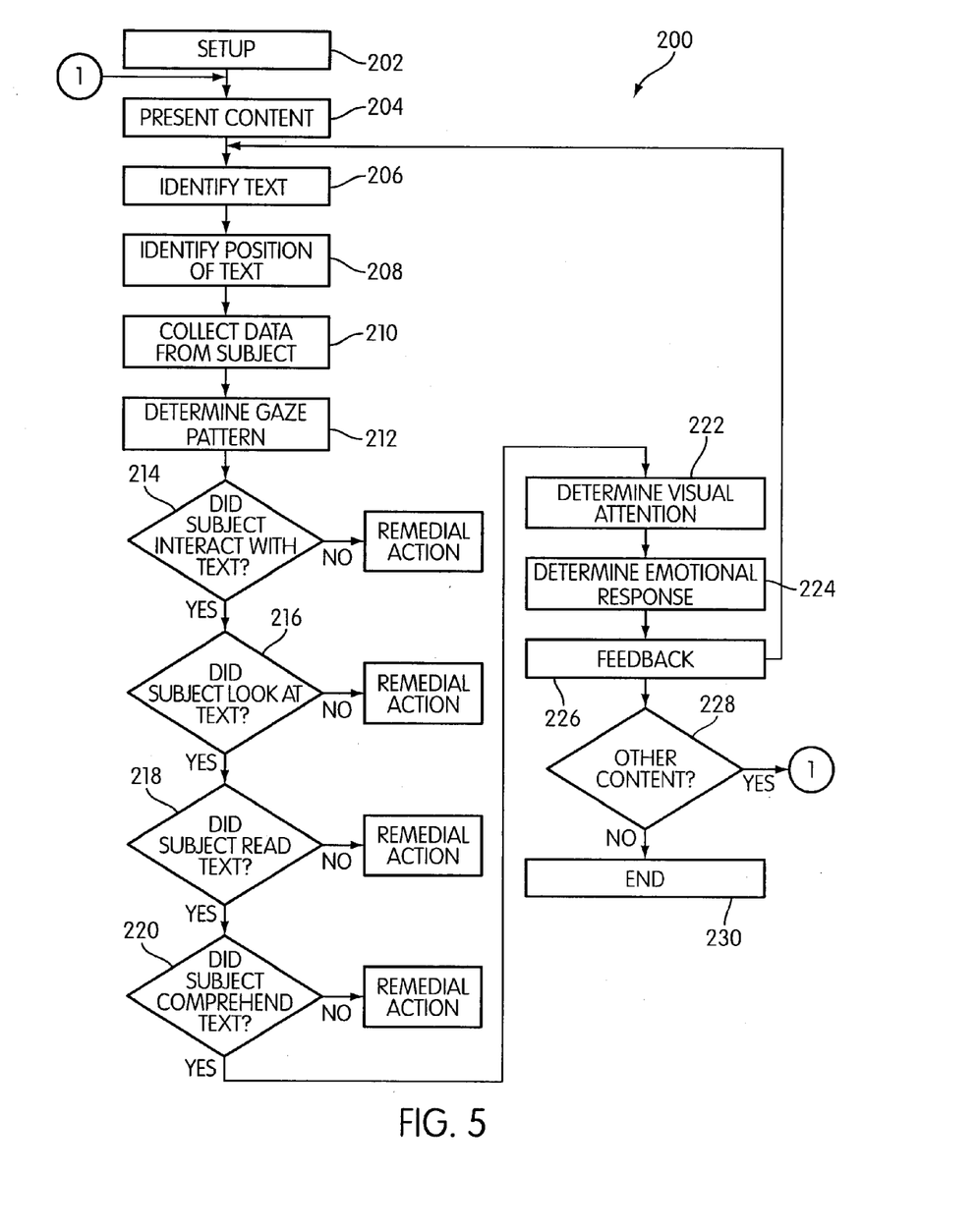
FIG. 5 is an exemplary illustration of a flowchart of processing operations, according to an aspect of the invention.

FIG. 5 illustrates an exemplary flowchart 200 of processing operations, according to an aspect of the invention. The described operations may be accomplished using some or all of the system components described in detail above and, in some implementations, various operations may be performed in different sequences. In other implementations, additional operations may be performed along with some or all of the operations shown in FIG. 5. In yet other implementations, one or more operations may be performed simultaneously. Accordingly, the operations described are exemplary in nature and, as such, should not be viewed as limiting.

In an operation 202, various preliminary (or setup) operations may be performed (e.g., performed by initial setup module 128).

In an operation 204, visual media content may be displayed to a subject (or user) (e.g., via display 162). The visual media content may include various display elements, at least a portion of which may include text.

Assuming that the visual media content includes at least a portion of text, the existence of text may be identified in an operation 206, and the position of the text (e.g., absolute or relative to other display elements) in the visual media content may be determined in an operation 208. Characteristics of the text (e.g., text character height, text character width, text character font, number of letters, number of words, length of words, length of lines of text, number of lines of text, etc.) may also be determined in either or both of operation 206 and 208. In one implementation, operations 206 and 208 may be performed, for example, by the text identification and position determination module 122.

The text identification and position determination module 122 may perform operations 206 and/or 208 when the visual media content is presented, or before or after presentation. As detailed below, in one implementation, data generated regarding a subject's interactions with the identified text (e.g., by text interaction determination module 126) and/or subject's emotional response to the identified text (e.g., by emotional response determination module 152a) may be provided back to the text identification and position determination module 122 as input to refine the text identification and position determination.

In an operation 210, various eye property data may be acquired from a subject positioned before display 162 (e.g., by eye tracking device 160). Collection of the eye property data may be governed by data collection module 132. The eye data, collected at a predetermined sampling rate, may include eye position data, eye blink data, pupil dilation data, and/or other eye data. Other physiological data, and/or other data from the subject may also be acquired in operation 210 (and governed by data collection module 132). Data concerning one or more physiological attributes of the subject may be collected from one or more emotion detection sensors. Data indicative of one or more environmental parameters (e.g., light intensity, noise, temperature, or other parameters) may also be acquired.

In an operation 212, the eye data collected (and/or other collected information) may be utilized, for example, by the eye gaze pattern determination module 124 to determine the eye gaze pattern of the subject.

The text identification and position data, the eye gaze pattern data, and/or other collected data, may be provided as input to the text interaction determination module 126. The text interaction determination module 126 may, in an operation 214, make a determination as to whether the subject has interacted with the identified text. If a determination is made that the subject interacted with the identified text at some level, processing may continue at operation 216. If a determination is made that the subject did not interact with the text, some remedial action or other action may be taken.

In an operation 216, the text interaction determination module 126 may determine whether the subject looked at the identified text. If the text interaction determination module 126 determines that, for example, at least a portion of the subject's eye gaze pattern overlaps with the coordinate positions of identified text in the document, the text interaction determination module 126 may determine that the subject has interacted with the identified text, at least to some extent. This may mean that, at a minimum, the subject looked at the identified text, and processing may continue with operation 218. If a determination is made that the subject did not look at the text, some remedial action or other action may be taken.

In operation 218, a determination may be made as to whether the subject read the identified text (e.g., by reading determination module 126a as described above). If a determination is made that the subject read the text, processing may continue at operation 220. If a determination is made that the subject did not read the text, some remedial action or other action may be taken.

In an operation 220, a determination may be made as to whether the subject comprehended the identified text (e.g., by comprehension determination module 126b). If a determination is made that the subject comprehended the text, processing may continue at operation 222. If a determination is made that the subject did not comprehend the text, some remedial action or other action may be taken.

According to an aspect of the invention, if desired, visual attention and/or emotional response information may also be determined for a subject that has viewed (or is currently viewing) visual media content.

In an operation 222, visual attention information for the subject may be determined (e.g., by visual attention determination module 152b).

Information regarding the subject's emotional responses to the visual media content, one or more portions of the identified text, and/or other portions of the visual media content may be determined in an operation 224 (e.g., by emotional response determination module 152a).

According to an aspect of the invention, in an operation 226, feedback regarding the subject's interactions with the identified text (e.g., by text interaction determination module 126) and/or the subject's emotional response to the identified text (e.g., emotional response determination module 152a) may be provided to the text identification and position determination module 122 to refine the text identification and position determination.

For example, if it is determined in operation 218 that the subject has read various text portions in the document, this information may indicate the positions of the text versus non-text (e.g. images, and/or other non-text portions) portions in the document. Such information may be provided as feedback to the text identification and position determination module 122 to further refine the text identification and position determination.

Although FIG. 5 depicts feedback being provided after processing of operation 226, it will be readily appreciated that the feedback may be provided after performing one or more of operations 212, 214, 216, 218, 220, 222, and/or 224.

In an operation 228, it may be determined if additional visual media content is to be presented to the subject. If it is determined that additional visual media content is to be presented to the subject, processing may resume at operation 204. If it is determined that no additional visual media content is to be presented to the subject, processing may end at operation 230.

Implementations of the invention may be made in hardware, firmware, software, or various combinations thereof. The invention may also be implemented as computer-readable instructions stored on a computer-readable storage medium which may be read and executed by one or more processors. A computer-readable storage medium may include various mechanisms for storing information in a form readable by a computing device. For example, a computer-readable storage medium may include read only memory, random access memory, magnetic disk storage media, optical storage media, flash memory devices, and/or other storage mediums. Further, firmware, software, routines, or instructions may be described in the above disclosure in terms of specific exemplary aspects and implementations of the invention, and performing certain actions. However, it will be apparent that such descriptions are merely for convenience, and that such actions may in fact result from computing devices, processors, controllers, or other devices executing firmware, software, routines or instructions.

Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A computer-implemented method of determining a subject's level of interaction with text in visual media content, the method being implemented by a computer that includes a physical processor, the method comprising:
    obtaining, by the computer, information regarding a position of identified text in a portion of visual media content;
    obtaining, by the computer, eye data associated with a subject's viewing of the visual media content, the eye data including pupil data, blink data, and gaze data;
    generating, by the computer, a gaze pattern of the subject based on the eye data;
    determining, by the computer, whether the subject has interacted with the identified text based at least on the position of the identified text and the generated gaze pattern; and
    in response to a determination that the subject has interacted with the identified text:
    (i) determining the subject's level of interaction with the identified text; and
    (ii) determining the subject's emotional response to the identified text.

2. The computer-implemented method of claim 1, wherein determining the subject's level of interaction with the identified text further comprises:
    determining whether the subject has read the identified text; and
    determining whether the subject has comprehended the identified text.

3. A computer-implemented system for determining a subject's level of interaction with text in visual media content, the system comprising:
    a computer comprising a physical processor configured to:
        obtain information regarding a position of identified text in a portion of visual media content;
        obtain eye data associated with a subject's viewing of the visual media content, the eye data including pupil data, blink data, and gaze data;
        generate a gaze pattern of the subject based on the eye data;
        determine whether the subject has interacted with the identified text based at least on the position of the identified text and the generated gaze pattern; and
        in response to a determination that the subject has interacted with the identified text:
        (i) determine the subject's level of interaction with the identified text; and
        (ii) determine the subject's emotional response to the identified text.

4. The computer-implemented system of claim 3, wherein to determine the subject's level of interaction with the identified text, the processor is further configured to:
    determine whether the subject has read the identified text; and
    determine whether the subject has comprehended the identified text.

5. A computer program product to determine a subject's level of interaction with text in visual media content, the computer program product comprising:
    one or more computer-readable tangible storage devices;
    program instructions, stored on at least one of the one or more computer-readable tangible storage devices, to:
        obtain information regarding a position of identified text in a portion of visual media content;
        obtain eye data associated with a subject's viewing of the visual media content, the eye data including pupil data, blink data, and gaze data;
        generate a gaze pattern of the subject based on the eye data;
        determine whether the subject has interacted with the identified text based at least on the position of the identified text and the generated gaze pattern; and
        in response to a determination that the subject has interacted with the identified text:
        (i) determining the subject's level of interaction with the identified text; and
        (ii) determining the subject's emotional response to the identified text.

* * * * *